United States Patent
Niedermeier

(10) Patent No.: US 10,074,169 B2
(45) Date of Patent: Sep. 11, 2018

(54) METHOD AND APPARATUS FOR DETECTING BUBBLES AND/OR CREASES ON LABELED CONTAINERS

(75) Inventor: Anton Niedermeier, Offenstetten (DE)

(73) Assignee: KRONES AG, Neutraubling (DE)

( * ) Notice: Subject to any disclaimer, the term of this patent is extended or adjusted under 35 U.S.C. 154(b) by 268 days.

(21) Appl. No.: 14/000,824

(22) PCT Filed: Jan. 10, 2012

(86) PCT No.: PCT/EP2012/000088
§ 371 (c)(1),
(2), (4) Date: Sep. 16, 2013

(87) PCT Pub. No.: WO2012/113492
PCT Pub. Date: Aug. 30, 2012

(65) Prior Publication Data
US 2014/0015960 A1      Jan. 16, 2014

(30) Foreign Application Priority Data
Feb. 23, 2011   (DE) .................... 10 2011 004 584

(51) Int. Cl.
*G06K 9/34*   (2006.01)
*H04N 7/18*   (2006.01)
(Continued)

(52) U.S. Cl.
CPC ........... *G06T 7/001* (2013.01); *G01N 21/909* (2013.01); *H04N 5/2256* (2013.01)

(58) Field of Classification Search
CPC ... G01N 21/896; G01N 21/9081; B65C 9/067
See application file for complete search history.

(56) References Cited

U.S. PATENT DOCUMENTS 5,729,340 A *  3/1998  Griesbeck et al. ........ 356/240.1
5,987,159 A    11/1999  Nichani
(Continued)

FOREIGN PATENT DOCUMENTS

EP   1985997 B1   1/2013
JP   3989739 B2   10/2007
(Continued)

OTHER PUBLICATIONS

International Search Report for PCT/EP2012/000088, dated May 14, 2012.
(Continued)

*Primary Examiner* — Rebecca Volentine
(74) *Attorney, Agent, or Firm* — Marshall, Gerstein & Borun LLP

(57) ABSTRACT

A method and an apparatus for detecting bubbles and/or creases on labeled containers. Bubbles/creases can be detected without comparison with a previously stored reference recording by virtue of the fact that a label to be examined is illuminated with a first flash of light, for example using the surface radiator, and is recorded in a first camera image, that the label is also illuminated with at least one second flash of light, for example using the directional radiator, with a changed directional characteristic and is recorded in a second camera image, and that a brightness difference between the first and second camera images is calculated.

18 Claims, 4 Drawing Sheets

(51) Int. Cl.
*G01N 21/00* (2006.01)
*G06T 7/00* (2017.01)
*G01N 21/90* (2006.01)
*H04N 5/225* (2006.01)

(56) References Cited

U.S. PATENT DOCUMENTS

| | | | | |
|---|---|---|---|---|
| 6,031,221 | A * | 2/2000 | Furnas | G01N 21/9036 209/524 |
| 6,259,827 | B1 * | 7/2001 | Nichani | G06T 7/0004 250/203.2 |
| 6,396,949 | B1 * | 5/2002 | Nichani | G06T 7/0004 250/203.2 |
| 7,626,158 | B2 * | 12/2009 | Diehr et al. | 250/223 B |
| 2001/0054680 | A1 * | 12/2001 | Lindner | G01N 21/9036 250/223 B |
| 2002/0195577 | A1 | 12/2002 | Gann et al. | |
| 2003/0112430 | A1 * | 6/2003 | Lindner | B07C 5/3408 356/239.4 |
| 2003/0142299 | A1 * | 7/2003 | Kwirandt | G01N 21/9027 356/239.5 |
| 2006/0045324 | A1 * | 3/2006 | Katayama | G01N 21/9054 382/142 |
| 2006/0208172 | A1 * | 9/2006 | Akkerman | G01N 21/9036 250/223 B |
| 2008/0230720 | A1 * | 9/2008 | Nielsen | 250/492.1 |
| 2008/0291438 | A1 * | 11/2008 | Akkerman et al. | 356/240.1 |
| 2010/0141756 | A1 * | 6/2010 | Grote et al. | 348/127 |
| 2010/0225908 | A1 * | 9/2010 | Kwirandt | 356/239.4 |
| 2010/0289892 | A1 * | 11/2010 | Kwirandt | G01N 21/9045 348/127 |
| 2010/0290695 | A1 * | 11/2010 | Kwirandt | B65C 9/067 382/142 |

FOREIGN PATENT DOCUMENTS

| | | |
|---|---|---|
| JP | 2008281477 A | 11/2008 |
| WO | WO-03104780 A1 | 12/2003 |

OTHER PUBLICATIONS

Notification of the Second Office Action for Application No. 201280018813.2, dated Jul. 27, 2015.

* cited by examiner

METHOD AND APPARATUS FOR DETECTING BUBBLES AND/OR CREASES ON LABELED CONTAINERS

CROSS-REFERENCE TO RELATED APPLICATION

The present application is the United States national phase of International Patent Application No. PCT/EP2012/000088, filed Jan. 10, 2012, which application claims priority to German Application No. DE 10 2011 004 584.8, filed Feb. 23, 2011. The entire text of the priority application is incorporated herein by reference.

FIELD OF THE DISCLOSURE

The Invention relates to a method and an apparatus for detecting bubbles and/or creases on labeled containers.

BACKGROUND

The inspection of labeled containers for intactness is usually done by imaging. For this, it is known, for example, from WO 03/104780 A1, to let a product stream composed of filled and labeled containers pass by an illuminated screen and to record the labels with a camera. Labels, being absorbent in the ultraviolet or infrared spectral range, produce a contrast against the filled bottle for detecting holes in the label.

JP 2008-281477 A further describes a method for inspecting transparent labels on transparent plastic bottles. By irradiation with ultraviolet light, fluorescence is excited in the labels, which can be represented as a difference in contrast to the non-fluorescent container. Holes and tears can thereby also here be detected as brightness differences in the fluorescence representation.

Unlike holes, bubbles and/or creases on labels cause relatively low contrasts in a representation by imaging, which is usually also overlaid with the necessarily high-contrast label prints. Bubbles and/or creases can therefore not be detected with sufficient reliability using a single camera image. Commercially available inspection apparatuses for bubbles and/or creases therefore draw on stored reference images of the label to be inspected.

However, numerous problems arise when operating such systems. For example, the label print quality among different label batches can vary, so that the reference recordings not only need to be updated regularly but also must be correctly assigned during operation. Since updating and teaching of the inspection apparatuses can not be fully automated, operator errors could possibly cause significant risks in quality control. In addition, the accuracy of the print and the labeling is critical for a comparison with previously stored images and therefore for reliable detection of bubbles and/or creases.

Furthermore, differently labeled products, such as with labels in different languages, involves an enormous effort due to frequent updating and teaching of such inspection systems. Overall, the administration of the reference images and the teaching involves a very high effort for maintenance and operation of the inspection systems and for the training of operating personnel. There is therefore a need to improve the known methods and apparatuses in this regard.

SUMMARY OF THE DISCLOSURE

The objective posed is satisfied with a method comprising the following steps: a) illuminating a label to be examined with a first flash of light and recording a first camera image of the label thus illuminated, b) illuminating the label with at least a second flash of light with a directional characteristic that is changed relative to step a) and recording at least a second camera image of the label thus illuminated, and c) calculating at least one brightness difference between the first and second camera image.

Due to the fact that two images were taken of one and the same label, storing a respective reference image in a database is unnecessary. Thereby, the need for updating reference images and the subsequent learning of bubble and/or crease detection is obsolete. Batch-related quality fluctuations of the label print and/or variations in the label position on the containers have no effect on the determination of brightness differences.

Due to the fact that at least two camera images are recorded with different directional illumination, elevations of the label, such as bubbles and/or creases can be displayed in the two camera images by shadows and/or lightened areas having different brightness. In contrast, a substantially smooth-surfaced label print can be displayed with at least similar brightness and/or contrast also when the directional characteristic of the light is changed, so that flat label areas, despite having a print, result in no or little brightness differences between the individual camera images. Thereby, calculated brightness differences between the first and the second camera image can be used as an indicator for the presence of a bubble and/or a crease on the label. In this, bubbles and/or creases are representative of all imperfections, compared to a properly affixed label, with which a shadow can be cast. This includes in particular projecting label sections at the label edges and/or holes in labels.

With the calculation, a comparison of brightness values and an assessment of brightness differences can be performed in an automated manner, for example, using standardized computational rules and/or a comparison with threshold values and/or predetermined brightness patterns, such as lines, letters, symbols and the like. As a result, bubbles and/or creases of label prints and/or relief structures can be distinguished on the label or in the labeled container.

A calculated brightness difference, for example, is to be understood as a difference in brightness values of corresponding image points and/or evaluation areas of the respective camera images to be compared. The difference could be evaluated, inter alia, using a calculated differentiation camera image or the like, for example, by contrast and/or pattern detection in the calculated image, and/or as a data record, for example by statistical evaluation of brightness values, or the like.

Flashes of light according to the present disclosure are to be understood as an arbitrary sequential succession of illumination states with different directional characteristics, if a sequential camera exposure is enabled. The illumination can therefore be pulsed arbitrarily or can be switched between different illumination states. However, flashes of light permit in particular maximization of the inspection speed desired in practice.

In a particularly advantageous embodiment, the directional characteristic in step a) and b) differs in terms of the proportion of diffuse illumination, in order to cast differently large shadows at bubbles and/or creases. Label prints can be displayed largely independently of the degree of diffusion of the illumination. In contrast, however, casting shadows and/or brightening occur at bubbles/creases with directional illumination in dependency of the direction of incidence, but not with diffuse illumination. Thereby, brightness differences between a camera image taken with diffuse illumination and a camera image taken with directional illumination incident from an angle can be used as a characteristic indicator for the detection of elevations on the label, such as bubbles or creases.

In an also advantageous embodiment, the directional characteristic in step a) and b) differs in terms of the main direction of incidence of the illumination for casting differently directed shadows at bubbles and/or creases. Label prints can be displayed in camera images largely independently of the direction of incidence of directional illumination. In contrast, displaying elevations of the label, such as creases and/or bubbles, depends relatively largely on the direction of incidence of directional illumination. In particular, the location of brightened areas and cast shadows at bubbles and/or creases depends on the direction of incidence of directional illumination. Thereby, brightness differences between the first and the second camera image, due to differing main directions of incidence, can be used as a characteristic indicator for the presence of a bubble and/or a crease on the label.

Brightness values of the first and the second camera image are in step c) in corresponding areas of the displayed label preferably offset against each other, wherein this off-setting comprises in particular a subtraction of the brightness values and/or an approximation of an average brightness of the first and the second camera image. Thereby, the influence of a label print can be very easily and effectively suppressed during the detection of bubbles/creases. Since the label print is displayed in the first and the second camera image in the same or a similar manner, subtraction of the camera images leads to a low-contrast display of differences of the label print. Adjustment of the average brightness of the first and the second camera image enables a particularly low-contrast display of differences.

The container is preferably being conveyed when recording the first and the second camera image. This makes it possible to inspect a continuous stream of products of labeled containers. The container is preferably moved relative to the illumination of the label and relative to the camera. However, it would also be possible to move the illumination and/or the camera, at least in sections, along with the container. The container is during inspection conveyed preferably linearly or along a circular path.

In a particularly advantageous embodiment, the first and the second camera image are taken at a time interval of at most 500 microseconds, in particular of at most 100 microseconds. As a result, two substantially identical images of the label to be examined can be taken with one camera. This means that the position and the perspective of the container in the image area of the camera section changes so slightly that the corresponding camera images of one and the same label can be offset against each other in a simple manner and at a great velocity.

Preferably, the label is illuminated with infrared light. Label prints under infrared illumination usually appear having less contrast than in the visible spectral range. In contrast, brightening and/or cast shadows on bubbles and/or creases are in the infrared and visible spectral range comparably strong in contrast. This results in a display with more contrast for brightenings and/or cast shadows under infrared illumination as compared to the label prints. Consequently, the label prints can for the evaluation of differences in brightness at bubbles and/or creases more easily be suppressed in the infrared spectral range, and bubbles/creases can be detected with greater reliability.

In a favorable embodiment, the illumination in step a) and b) differs with respect to its spectral range. In this manner, for example, in combination with different directions of incidence, a difference in brightness can be assessed in a qualitative manner at bubbles and/or creases and/or the plausibility of the examination can be assessed. For example, it can be ascertained whether the brightening in the first camera image corresponds to a cast shadow in the second camera image and/or is located in a relative position to be expected.

The object is also satisfied by an apparatus comprising an illumination device for sequentially illuminating a label to be examined with a first flash of light having a first directional characteristic and with at least a second flash of light having a directional characteristic differing therefrom; at least one camera for recording the label in at least one camera image with an illumination having a first directional characteristic and in at least a second camera image with an illumination having a second directional characteristic; and an evaluation unit for calculating at least one brightness difference between the first and the second camera image. It is possible to achieve the same advantages as with the method according to the invention.

Preferably, the illumination device comprises at least one surface radiator and/or multiple light sources for diffuse illumination of the label. Thereby, an illumination can be provided with which the label prints are evenly illuminated and bubbles and/or creases are displayed in low contrast. With surface radiators, such as fluorescent screens or light-emitting diode panels, diffuse irradiation can be provided in a particularly simple and compact manner. Several spatially distributed light sources when jointly operated are suited for diffuse illumination and when individually operated or as a group likewise for directional radiation.

Preferably, the illumination device comprises at least one directional radiator to cast a shadow on the label at bubbles and/or creases, in particular a substantially vertically cast shadow. Bubbles and/or creases can thereby be detected in a particularly reliable manner. A vertically cast shadow, i.e. substantially parallel to the main axis of the container, is particularly advantageous to examine the largest possible area of the label also on curved container walls. Moreover, label creases in practice often extending horizontally can be particularly reliably detected.

A particularly advantageous embodiment of the apparatus according to the present disclosure further comprises a conveyor device for conveying the container during imaging. This allows a continuous product stream of labeled containers to be examined, in particular, without having to interrupt or slow down the conveying movement. The conveyor device can for example be a linear conveyor or a carousel, for example, a labeling carousel. Rotatable supports can be provided on the conveyor device to perform the method according to the invention at different rotation positions of the container.

Preferably, the illumination device is for sequential camera exposures designed having an exposure interval of at most 500 microseconds, in particular of at most 100 microseconds. This allows two camera images to be taken with substantially identical container and label positions in the camera image as well as an identical image perspective. With the specific exposure intervals, high machine performance can be realized without compromising the reliability and the accuracy of the bubble and/or crease detection.

Preferably, at least two directional radiators are provided on the illumination device to create at least two shadows at the bubbles and/or creases cast in different directions, particularly in opposite and/or in orthogonal directions relative to each other. Differently shaped and/or oriented creases and bubbles can thereby be identified with very high reliability. In addition, a plausibility check of the detected bubbles and/or creases can be performed, with which detected brightening and cast shadows can be compared to each other. It can therefore in particular be examined whether the position of the cast shadows or brightening during sequential exposure with the directional radiators changes in an expected manner.

Preferred embodiments of the present disclosure are illustrated in the drawings.

DETAILED DESCRIPTION OF THE PREFERRED EMBODIMENTS

Figure 1:
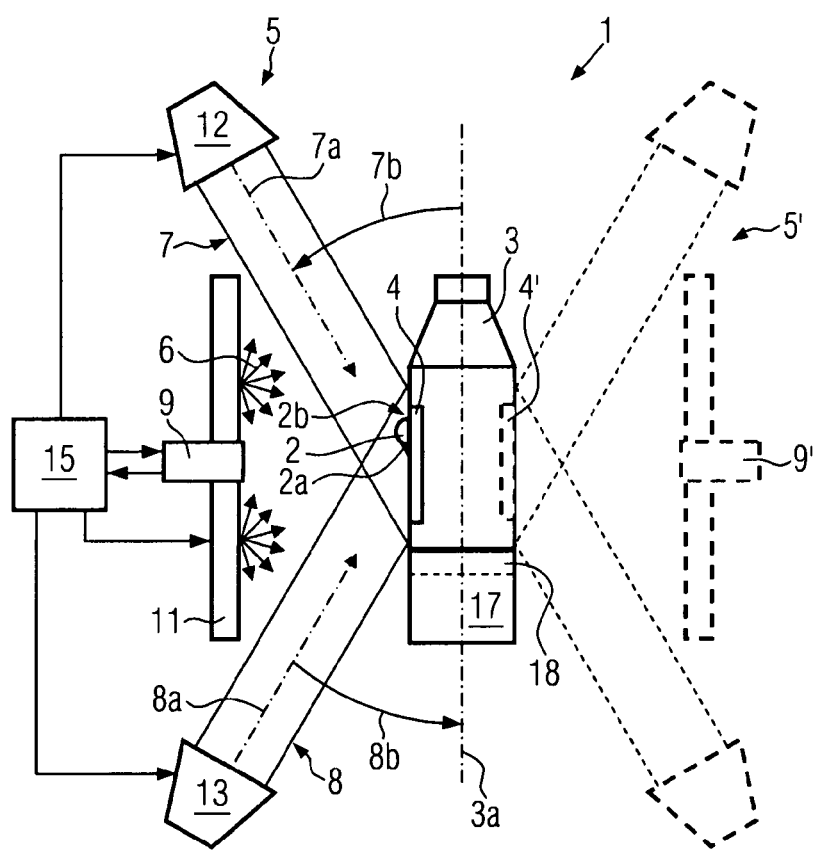
FIG. 1 shows a schematic cross-section through a first embodiment of the apparatus according to the present disclosure.

As shown in FIG. 1, the apparatus 1 according to the present disclosure in a first embodiment for detecting bubbles 2 and/or creases or the like (hereinafter also referred to merely as bubbles 2) on labels 4 attached to containers 3 comprises an illumination device 5 for selectively producing diffuse illumination 6 or directional illumination 7, 8 for incident light radiation to the label 4 and at least one camera 9 for displaying the label 4 illuminated with different directional characteristics. The camera 9 is, for example, a matrix camera with a flat sensor element. The containers 3, for example, are beverage bottles, in particular bottles made of PET.

For producing diffuse illumination 6, a surface radiator 11 is preferably provided, for example, a lamp having a diffusion screen or a light-emitting diode screen. But it would also be possible to spatially distribute any light sources such that the light emitted by the light sources on the label 4 adds to become a substantially diffuse illumination 6. For producing the directional illumination 7, 8, directional radiators 12, 13 are provided, where the main directions of incidence 7a, 8a of the directional illumination 7, 8 differ in the region of the label 4 in order to cast different shadows 2a at bubbles 2 on the label 4. This is indicated in FIG. 1, for illustration purposes only, for directional illumination 7 at an angle from above. Depending on the nature of the print 4a on the label 4, brightening 2b can at the bubbles 2 be created using directional illumination 7, 8, as shown, for example, in FIGS. 3 and 4.

Furthermore, an evaluation and control unit 15 is provided for controlling the illumination device 5 and the camera 9. The evaluation and control unit 15 also serves to read out and evaluate camera images B1, B2 produced by the camera 9, as shall be explained in more detail below with reference to FIGS. 3 and 4. In FIG. 1, signals and data streams for controlling and reading out are each symbolized by arrows. It is here understood that controlling and reading out as well as evaluating data can be done in separate units.

The apparatus 1 according to the invention further comprises a conveyor device 17 for continuously conveying the container 3 during label inspection, e.g. into the drawing plane shown in FIG. 1 or out of it. The conveyor device 17 can comprise a linear transport path 5 in the area of the illumination device 5 or rotate about a vertical axis, such as with a carrousel of a labeling machine. Rotatable supports 18 for the containers 3 can be provided at the conveyor device 17, for example, rotary plates or clamps to rotate the containers 3 between successive inspections about their main axis 3a. The rotatable supports 18 can, for example, be used to change over between two rotational positions of the container 3 offset by 180°. Therewith, a label 4 could first be examined and, upon changing the rotational position, an oppositely disposed second label 4', which is indicated by dashed lines in FIG. 1. During the inspection of one and the same label 4, 4', however, the rotational position of the container 3 is preferably not changed.

For two-sided inspection of the container 3, it is also conceivable to provide a further illumination device 5' and a further camera 9' on the opposite side of the conveyor device 17, as shown in FIG. 1 in dashed lines. In this case, labels 4, 4' could be inspected simultaneously on the front and the rear side of the container 3.

The apparatus shown in FIG. 1 is particularly well suited for detecting bubbles 2 and horizontally extending creases. For this purpose, the directional radiation 7, 8, is effected at an angle from above and/or at an angle from the below onto the label 4. The respective angles of incidence 7b, 8b between the main direction of incidence 7a, 8a and the main axis 3a of the container 3 is in this case preferably not larger than 45°. Angles 7b, 8b of 30° are particularly advantageous. This allows a shadow to be cast in a more pronounced manner at bubbles 2 and horizontal creases.

Figure 2:
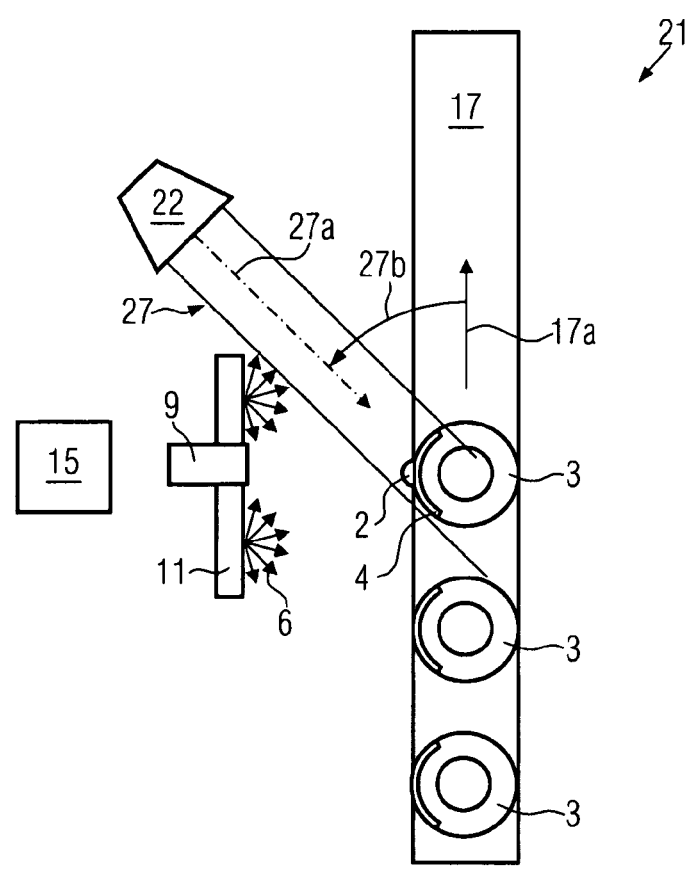
FIG. 2 shows a plan view of a second embodiment of the apparatus according to the present disclosure.

FIG. 2 shows a schematic plan view of a second embodiment 21 of the apparatus according to the present disclosure which is particularly suited for detecting bubbles 2 and vertically extending creases of the label 4. In this, the second embodiment 21 differs from the first embodiment 1 essentially only by the directional radiator 22 and the directional illumination 27 which, in this case, is incident at an angle from a lateral direction. The main direction of incidence 27a presently forms an angle 27b with the conveying direction 17a of the conveyor device that is preferably not greater than 45°. Furthermore, the main direction of incidence 27a extends preferably, but not necessarily, horizontally, also orthogonally to the container main axis 3a.

The directional radiators 12, 13 and 22 shown in FIGS. 1 and 2 and the associated main directions of incidence 7a, 8a, 27a, however, are merely by way of example. According to the present disclosure, any combinations of different directional illuminations for recording the images of the label 4 are possible, both in terms of the respective main direction of incidence as well as the proportion of diffuse light and/or the beam divergence. The decisive factor is an exposure of at least two mutually corresponding camera images B1, B2 of the label 4 with differently oriented label illumination.

Preferably, the label 4 is respectively displayed in the camera images B1, B2 entirely and possibly within matching image areas. But only a certain label area of particular interest can also be displayed. Since the container 3 is moved during inspection of the label with the conveyor device 17, camera images B1, B2 of a label 4 to be compared to each other should be recorded with a minimum time interval. Time intervals of at most 500 microseconds are particularly advantageous, in particular at most 100 microseconds between corresponding exposures of the label 4. It is then possible, for example, to buffer the first camera image B1 in the matrix sensor of the camera 9 and to record the second camera image B2 before the first camera image B1 has been read out.

Exposure with the different directional illuminations 6, 7, 8, 27 is sequential and performed preferably with a time-coordinated sequence of flashes of light, in particular in the form of at least a double-flash. It can, for example, be composed of a diffuse flash and a directional flash. Such pulsed illuminations 6, 7, 8, 27 are preferably produced with light-emitting diodes. The illumination device 5 can be controlled such that the surface radiator 11 first emits a first exposure flash, and then the upper directional radiator 12 emits a second exposure flash, or vice versa. It would also be conceivable, that the upper directional radiator 12 and the lower directional radiator 13 each emit an exposure flash. Depending on the container shape, the label print, the shape and orientation of bubbles 2 and/or creases, any sequential combination of diffuse and/or directional illumination 6, 7, 8, 27 is conceivable. It is crucial that the exposure conditions of the camera images B1, B2 differ from each other. This is achieved by varying directivity and the temporal interval of the illumination 6, 7, 8, 27 employed.

The illumination 6, 7, 8, 27 is preferably effected with infrared light to achieve a particularly favorable signal ratio between the cast shadows 2a, brightenings 2b, and the differences in contrast caused by the label print 4a. It is also conceivable to expose the camera 9 for the camera images B1, B2 to light of different spectral ranges, so that the shadows 2a and brightenings 2b produced in the respective spectral regions 2a can be recorded separately, for example, by filtering and/or selective image processing.

The described embodiments 1, 21 of the apparatus according to the present disclosure can be arbitrarily combined in order to be able to particularly reliably detect, for example, bubbles 2 and creases extending in any direction. The embodiments 1 to 21 can also be arranged at different sections of the production line.

Although the illuminations 6, 7, 8, 27 for the exposure of the camera images B1, B2 differ with respect to the their directional characteristic, it is nevertheless desirable to illuminate the label 4 as much as possible at a constant overall brightness and brightness distribution in order to display the label print 4a in the corresponding camera images B1, B2 as identically as possible. By simple image processing and/or by calculating the difference of image areas of the camera images B1, B2 corresponding to each other, the label print 4a can be suppressed for detecting the bubbles 2 and/or creases. This is described below with reference to two variants of the method according to the present disclosure:

A continuous product stream of labeled containers 3 is conveyed by the conveyor device 17 through the inspection apparatus 1, 21 according to the invention and the labels 4 are there illuminated in a short sequence of flashes of light having different directional characteristics and displayed by the camera 9 in respectively at least one camera image B1, B2. It is presently understood that any number of corresponding camera images of the same label 4 can be recorded and evaluated.

Figure 3:
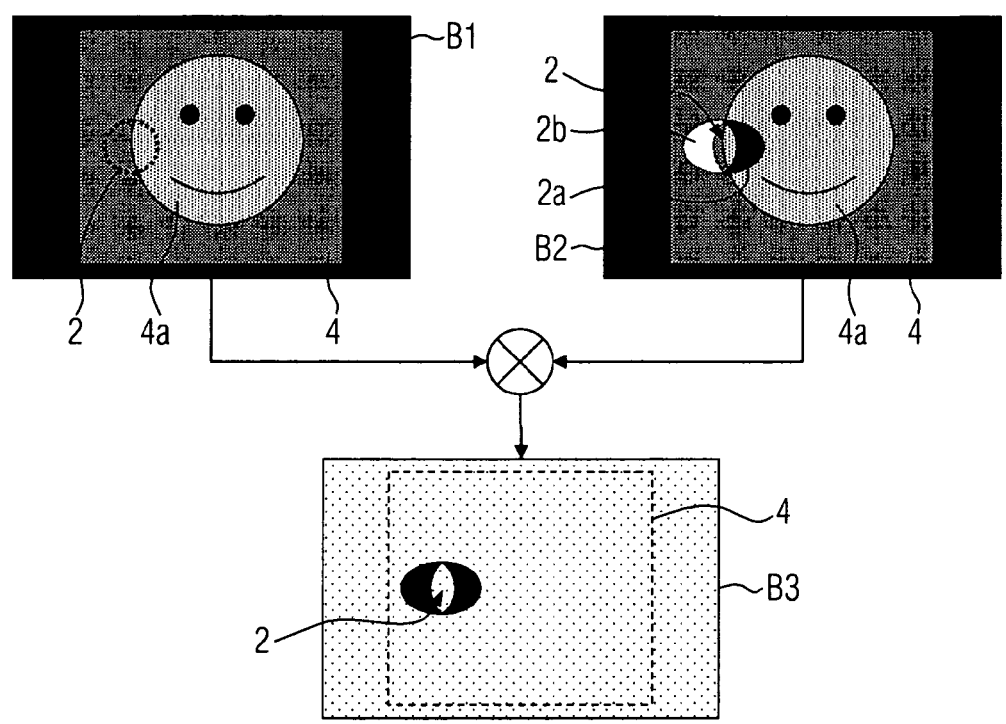
FIG. 3 shows a schematic representation of the method of the present disclosure according to a first variant.

In FIG. 3, corresponding camera images B1, B2 are displayed schematically as they could be recorded, for example, with the second embodiment 21. According thereto, the first camera image B1 is exposed with the diffuse illumination 6, so that the bubble 2 indicated with a dotted line is not displayed in the camera image B1 or only with a very low contrast difference. The label print 4a, however, is at diffuse illumination 6 displayed with high contrast.

With a time interval of preferably no more than 100 microseconds, the control unit 15 triggers the directional illumination 27 at the directional radiator 22 in the form of a second flash of light with which the label 4 is illuminated at an angle from a lateral direction in order to cast a shadow 2a at the bubble 2. As also shown in FIG. 3, brightening is additionally created at the bubble 2. Moreover, the directional illumination 27 is also formed such that the label print 4a is shown in high contrast.

The diffuse illumination 6 and the directional illumination 27 can be matched to as much correspondence as possible regarding the illumination of the label print 4a, so that the latter is displayed in the corresponding camera images B1, B2 with substantially matching or at least similar brightness values Likewise, the recorded camera images B1, B2 can be processed for matching, for example, by adaptation of brightness and/or contrast adjustment and/or by filtering. Corresponding image areas of the camera images B, B2 can then be offset against each other, for example, by calculating the difference of brightness values of corresponding image points or evaluation areas of the camera images B1, B2. Thereby, the label print 4a can be effectively suppressed for detecting bubbles 2 and/or creases in a camera image B3 calculated based on corresponding camera images B1, B2.

In contrast, the bubble 2 in the second camera image B2 is outlined in high contrast by the cast shadow 2a and the brightening 2b. When offsetting the corresponding camera images B1, B2, this difference in contrast in the area of bubble 2 essentially remains in the calculated camera image B3, whereas the label print 4a is suppressed. This is indicated as the calculation result in the calculated camera image B3 of FIG. 3 as a dark crescent-shaped outline of the bubble 2. For the evaluation of the corresponding camera images B1, B2, it is irrelevant whether a cast shadow 2a or brightening 2b as a calculation result is ultimately shown light or dark. For example, the cast shadow 2a can be inverted for the evaluation or the brightening 2b. Offsetting corresponding camera images B1, B2 can be adapted to almost any different label prints, such as very bright, dark or high-contrast prints for effectively suppressing them and identifying bubbles 2.

For the evaluation, a threshold value can be set with which the calculation result, i.e. for example brightness values of the calculate camera image B3, is compared. A certain number of image points whose brightness value exceeds the threshold value could then be a characteristic indicator of the presence of a bubble 2 and/or crease. Geometric patterns, characters or symbols are also conceivable as the criterion for comparison of a group of image points whose brightness is given within a certain range. For this, almost any computing rules are generally conceivable which can be flexibly adapted to different types of labels, prints, container shapes and the like.

Figure 4:
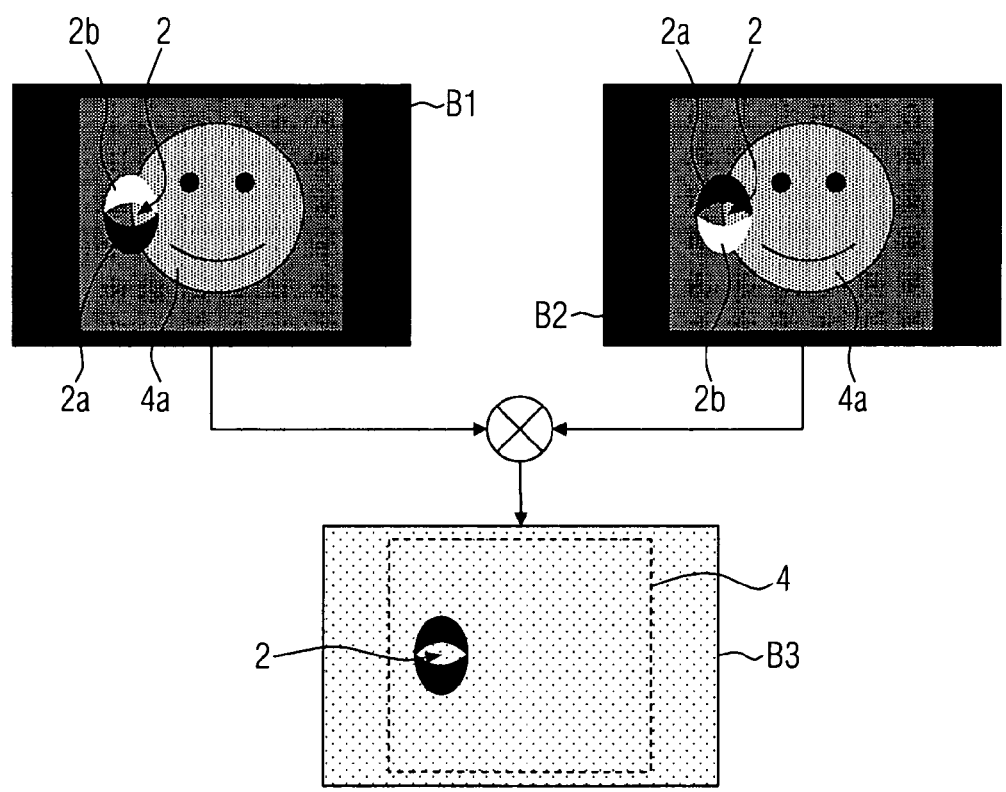
FIG. 4 shows a schematic representation of the method of the present disclosure according to a second variant.

FIG. 4 illustrates a variant as it could be implemented, for example, with the first embodiment 1. An example is shown in which the first camera image B1 is recorded with directional illumination 7 at an angle from above, for example, with the directional radiator 12, and the second camera image B2 with directional illumination 8 at an angle from below, for example, with the directional radiator 13. Also in this case, the illuminations are designed such that the label print 4a can be suppressed when being offset. The positions of the cast shadow 2a and the brightening 2b in the two camera images B1, B2 correspond to each other in mirror-image. This could be used for additional plausibility checks. For example, to check whether the position of the cast shadow 2a in the first camera image B1 corresponds to the position of the brightening 2b in the second camera image B2.

It is crucial for the method according to the present disclosure, that at least two corresponding camera images B1, B2 are recorded in which the label print 4a is displayed such that it can be suppressed by offsetting the two camera images B1, B2 for detecting bubbles 2 and/or creases, and which differ in terms of at least one brightening 2b or one shadow 2a produced or cast by the bubble/crease 2.

Calculating the difference of the camera images B1, B2 is for instance suited as an evaluation. In addition, the brightness and/or the contrast of the individual camera images B1, B2 can be adjusted. It is not necessary to completely suppress the label print 4a in the calculated camera image B3. In this, it is sufficient to suppress remaining differences in contrast of the label print 4a in the calculated camera image B3 below a predetermined threshold value, such that differences in contrast resulting from a bubble 2 and/or a crease in the calculated camera image B3 are above the threshold value, and therefore can be distinguished from the label print.

As is illustrated in FIGS. 3 and 4, the method according to the present disclosure allows in particular detection of bubbles 2 and/or creases that are overlaid with a high-contrast label print 4a.

The time interval between the first and the second camera image B1, B2 is so short that the label 4 to be examined or the label area to be examined, respectively, is imaged entirely by the camera 9. Preferably, the time interval is so small that the label 4 in the corresponding camera images B1, B2 is displayed in an identical image position. In this, however, it is also conceivable that the label 4 is between the camera images B1, B2 moved by a known lateral displacement, for example, by one or several image points, so that the camera images B1, B2 can be offset against each other taking into account the lateral displacement. The image position of the label 4 in the corresponding camera images B1, B2 corresponds in at least that similar imaging conditions arise, such as perspective distortion and the like, so that an offset and an evaluation of corresponding label areas of the camera images B1, B2 is possible in real time.

While offsetting only two corresponding camera images B1, B2 was described, several corresponding camera images could of course be offset against each other in accordance with the invention, as long as the sequential exposure according to the present disclosure with different directional characteristics is given.

The described embodiments of the method and the apparatus according to the invention are suitable for inspecting different types of containers, which, for example, can also be made of glass or plastic, for example, PET, PE, HDPE, but also of metal such as aluminum, or of composite material. Likewise, the containers can contain different contents, for example, beverages such as juices, milk, mineral water, beer and the like, as well as bulk goods, such as coffee, pills and the like. It goes without saying that the contents are not limited to foods. Inter alia, medicines, toiletries, cleaning articles, detergents and the like are possible.

The shape of the container to be inspected is not limited to the convex cross-sections mentioned, in particular not the round ones. Suitable are also flat or concave surfaces and containers with polygonal or oval bottoms and/or cross-sections.

Moreover, not only bubbles or creases can be detected. The apparatuses and methods described are also suitable for a checking the correct attachment of labels onto containers.

For example, projecting label edges, uneven gluing points, damages such as holes, in particular, for sleeve labels, can be detected if the label material extends in an improper manner from the container.

In general, all elevated irregularities or defects at can be detected at any location on the container provided that a shadow can be cast there by directional illumination. However, the invention is particularly suitable for detecting irregularities or defects on printed labels, in particular due to an improved differentiation vis-a-vis high-contrast prints.

Various types of labels can be inspected, for example, paper labels, plastic labels, round labels, sleeves, shrink labels, stretch labels and the like.

The invention claimed is:

1. Method for detecting at least one of bubbles and creases on labeled containers, the method comprising:
   a) illuminating an outer surface of a label to be examined with a first flash of incident light from a first light source and recording a first camera image of said label thus illuminated with a camera;
   b) illuminating an outer surface of said label with at least a second flash of incident light from a second light source, wherein the second flash of incident light has a directional characteristic that is changed relative to that of the first flash of incident light and recording at least a second camera image of said label thus illuminated with the camera, wherein (i) the first flash of incident light has a first direction of illumination, from above, that is no more than 45° relative to a vertical axis containing the label and the second flash of incident light is diffuse illumination, (ii) the first flash of incident light has a first direction of illumination, from below, that is no more than 45° relative to a vertical axis containing the label and the second flash of incident light is diffuse illumination, or (iii) the first flash of incident light has a first direction of illumination, from above, that is no more than 45° relative to a vertical axis containing the label, and the second flash of incident light has a second direction of illumination, from below, that is no more than 45° relative to a vertical axis containing the label; and
   c) calculating at least one brightness difference between said first and second camera image,
   wherein the order of the first flash of incident light and the second flash of incident light is arbitrary, and
   wherein a time interval between said first camera image and said second camera image is at most 500 microseconds.

2. Method according to claim 1, wherein said directional characteristic in a) and b) differs in terms of a proportion of diffuse illumination in order to cast differently large shadows at the at least one of bubbles and creases.

3. Method according to claim 1, wherein the first light source is configured to produce the first flash of incident light having the first direction of illumination for casting differently directed shadows at the at least one of bubbles and creases than from the second light source configured to produce the second flash of incident light.

4. Method according to claim 1, wherein brightness values of said first and said second camera image in c) are in corresponding areas of said label offset against each other.

5. Method according to claim 1, wherein said calculated brightness differences are further compared to at least one threshold value to differentiate between a label print and a bubble/crease.

6. Method according to claim 1, wherein said container is being conveyed when recording said first and said second camera image.

7. Method according to claim 1, wherein said label is illuminated with infra-red light.

8. Method according to claim 1, wherein the first flash of incident light and the second flash of incident light differ in spectral range.

9. Apparatus for detecting at least one of bubbles and creases on labeled containers, the apparatus comprising:
- an illumination device for sequentially illuminating an outer surface of a label to be examined with a first flash of incident light having a first directional characteristic and with at least a second flash of incident light having a directional characteristic differing therefrom, wherein (i) the first flash of incident light has a first direction of illumination, from above, that is no more than 45° relative to a vertical axis containing the label and the second flash of incident light is diffuse illumination, (ii) the first flash of incident light has a first direction of illumination, from below, that is no more than 45° relative to a vertical axis containing the label and the second flash of incident light is diffuse illumination, or (iii) the first flash of incident light has a first direction of illumination, from above, that is no more than 45° relative to a vertical axis containing the label, and the second flash of incident light has a second direction of illumination, from below, that is no more than 45° relative to a vertical axis containing the label;
- a camera for recording said label in at least one camera image with an illumination having said first directional characteristic and in at least a second camera image with an illumination having said second directional characteristic; and
- an evaluation unit for calculating at least one brightness difference between said first and said second camera image,
- wherein the order of the first flash of incident light and the second flash of incident light is arbitrary, and wherein a time interval between said first camera image and said second camera image is at most 500 microseconds.

10. Apparatus according to claim 9, where said illumination device comprises at least one of a surface radiator and multiple light sources for diffuse illumination of said label.

11. Apparatus according to claim 9, where said illumination device comprises at least one directional radiator to cast a shadow onto said label at the at least one of bubbles and creases.

12. Apparatus according to claim 9, further comprising a conveyor device to convey said container during imaging.

13. Apparatus according to claim 9, where at least two directional radiators are provided on said illumination device to create at least two shadows at the at least one of bubbles and creases cast in different directions, wherein at least one of the directional radiators is configured to produce the first flash of incident light along the first direction of illumination and at least one other of the directional radiators is configured to produce the second flash of incident light.

14. Apparatus according to claim 9, wherein said illumination device is for sequential camera exposures having an exposure interval of at most 100 microseconds.

15. Apparatus according to claim 13, wherein the different directions include at least one of opposite and orthogonal directions relative to each of the shadows.

16. Method according to claim 4, wherein said offsetting comprises at least one of subtraction of said brightness values and an approximation of an average brightness of said first and said second camera image.

17. Method according to claim 1, wherein the time interval between said first and said second camera image is at most 100 microseconds.

18. Apparatus according to claim 11, wherein the at least one directional radiator casts a substantially vertically shadow onto said label at the at least one of bubbles and creases.

* * * * *